US007722536B2

(12) United States Patent  
Goodnow

(10) Patent No.: US 7,722,536 B2
(45) Date of Patent: May 25, 2010

(54) GLUCOSE MEASURING DEVICE INTEGRATED INTO A HOLSTER FOR A PERSONAL AREA NETWORK DEVICE

(75) Inventor: Timothy T. Goodnow, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1184 days.

(21) Appl. No.: 10/891,327

(22) Filed: Jul. 14, 2004

(65) Prior Publication Data

US 2009/0048501 A1  Feb. 19, 2009

(51) Int. Cl.
*A61B 5/00* (2006.01)

(52) U.S. Cl. .......................... 600/365; 600/347

(58) Field of Classification Search ......... 600/345–347, 600/365
See application file for complete search history.

(56) References Cited

U.S. PATENT DOCUMENTS

| 5,349,852 | A | 9/1994 | Kamen et al. |
| 5,376,070 | A | 12/1994 | Purvis et al. |
| 5,472,317 | A | 12/1995 | Field et al. |
| 5,489,414 | A | 2/1996 | Schreiber et al. |
| 5,526,844 | A | 6/1996 | Kamen et al. |
| 5,533,389 | A | 7/1996 | Kamen et al. |
| 5,601,435 | A | 2/1997 | Quy |
| 5,665,065 | A | 9/1997 | Colman et al. |
| D393,313 | S | 4/1998 | Meisner et al. |
| 5,735,285 | A | 4/1998 | Albert et al. |
| 5,772,586 | A * | 6/1998 | Heinonen et al. ........... 600/300 |
| 5,791,344 | A * | 8/1998 | Schulman et al. ........... 600/347 |
| 5,822,715 | A | 10/1998 | Worthington et al. |
| 5,899,855 | A | 5/1999 | Brown |
| 5,918,603 | A | 7/1999 | Brown |
| 5,956,501 | A | 9/1999 | Brown |
| 5,961,451 | A | 10/1999 | Reber et al. |
| 6,159,147 | A | 12/2000 | Lichter et al. |
| 6,175,752 | B1 * | 1/2001 | Say et al. ................... 600/345 |
| 6,233,539 | B1 | 5/2001 | Brown |
| 6,283,761 | B1 | 9/2001 | Joao |

(Continued)

FOREIGN PATENT DOCUMENTS

WO   WO-03/049597   6/2003

(Continued)

*Primary Examiner*—Patricia C Mallari
*Assistant Examiner*—Karen E Toth
(74) *Attorney, Agent, or Firm*—Jackson & Co., LLP

(57) ABSTRACT

A glucose meter module integrated into a holster device that can securely accommodate another device such as a portable server device or an insulin pump is described. The glucose measuring module and the health device communicate with each other by a short range wireless modality. In the case in which the accommodated device is a server, such as personal digital assistant or cell phone, the device stores data in a memory, displays data on a visual display, and can wirelessly transmit such data to other devices within a personal area network. In the case where the accommodated device is a cell phone, the phone can further transmit data to remote sites. In the case where the accommodated device is an insulin pump, wirelessly received data are stored in a memory, are available for visual display on the insulin pump, and can be incorporated into the electronic processes that regulate the performance of the pump.

19 Claims, 8 Drawing Sheets

U.S. PATENT DOCUMENTS

| | | | |
|---|---|---|---|
| 6,348,640 B1 | 2/2002 | Navot et al. | |
| 6,359,444 B1 | 3/2002 | Grimes | |
| 6,379,301 B1 | 4/2002 | Worthington et al. | |
| 6,396,416 B1* | 5/2002 | Kuusela et al. | 340/870.28 |
| 6,428,475 B1* | 8/2002 | Shen | 600/300 |
| 6,485,461 B1 | 11/2002 | Mason et al. | |
| 6,558,320 B1* | 5/2003 | Causey et al. | 600/300 |
| 6,558,321 B1 | 5/2003 | Burd et al. | |
| 6,560,471 B1* | 5/2003 | Heller et al. | 600/347 |
| 6,561,978 B1* | 5/2003 | Conn et al. | 600/309 |
| 6,656,158 B2 | 12/2003 | Mahoney et al. | |
| 6,656,159 B2 | 12/2003 | Flaherty | |
| 6,669,669 B2 | 12/2003 | Flaherty et al. | |
| 6,692,457 B2 | 2/2004 | Flaherty | |
| 6,699,218 B2 | 3/2004 | Flaherty et al. | |
| 6,702,857 B2 | 3/2004 | Brauker et al. | |
| 6,723,072 B2 | 4/2004 | Flaherty et al. | |
| 6,740,059 B2 | 5/2004 | Flaherty | |
| 6,741,877 B1 | 5/2004 | Shults et al. | |
| 6,749,587 B2 | 6/2004 | Flaherty | |
| 6,752,299 B2 | 6/2004 | Shetler et al. | |
| 6,768,425 B2 | 7/2004 | Flaherty et al. | |
| 6,830,558 B2 | 12/2004 | Flaherty et al. | |
| 6,862,465 B2 | 3/2005 | Shults et al. | |
| 6,916,159 B2 | 7/2005 | Rush et al. | |
| 6,931,327 B2 | 8/2005 | Goode, Jr. et al. | |
| 6,942,518 B2 | 9/2005 | Liamos et al. | |
| 6,960,192 B1 | 11/2005 | Flaherty et al. | |
| 7,003,335 B2* | 2/2006 | Briancon | 455/575.6 |
| 7,018,360 B2 | 3/2006 | Flaherty et al. | |
| 7,029,455 B2 | 4/2006 | Flaherty | |
| 7,041,468 B2* | 5/2006 | Drucker et al. | 435/14 |
| 7,052,251 B2 | 5/2006 | Nason et al. | |
| 7,074,307 B2 | 7/2006 | Simpson et al. | |
| 7,081,195 B2 | 7/2006 | Simpson et al. | |
| 7,108,778 B2 | 9/2006 | Simpson et al. | |
| 7,110,803 B2 | 9/2006 | Shults et al. | |
| 7,134,999 B2 | 11/2006 | Brauker et al. | |
| 7,136,689 B2 | 11/2006 | Shults et al. | |
| 7,137,964 B2 | 11/2006 | Flaherty | |
| 7,144,384 B2 | 12/2006 | Gorman et al. | |
| 7,156,809 B2* | 1/2007 | Quy | 600/301 |
| 7,167,818 B2 | 1/2007 | Brown | |
| 7,192,450 B2 | 3/2007 | Brauker et al. | |
| 7,226,278 B2 | 6/2007 | Nason et al. | |
| 7,226,978 B2 | 6/2007 | Tapsak et al. | |
| 7,258,673 B2* | 8/2007 | Racchini et al. | 600/583 |
| 7,259,681 B2* | 8/2007 | Kwoen | 340/573.1 |
| 7,276,029 B2 | 10/2007 | Goode, Jr. et al. | |
| 7,278,983 B2* | 10/2007 | Ireland et al. | 604/66 |
| 7,303,549 B2 | 12/2007 | Flaherty et al. | |
| 7,310,544 B2 | 12/2007 | Brister et al. | |
| 7,399,277 B2* | 7/2008 | Saidara et al. | 600/300 |
| 2001/0025189 A1 | 9/2001 | Haueter et al. | |
| 2002/0107476 A1 | 8/2002 | Mann et al. | |
| 2002/0128594 A1 | 9/2002 | Das et al. | |
| 2003/0023317 A1 | 1/2003 | Brauker et al. | |
| 2003/0023461 A1 | 1/2003 | Quintanilla et al. | |
| 2003/0032867 A1 | 2/2003 | Crothall et al. | |
| 2003/0032874 A1 | 2/2003 | Rhodes et al. | |
| 2003/0078481 A1* | 4/2003 | McIvor et al. | 600/347 |
| 2003/0088238 A1 | 5/2003 | Poulsen et al. | |
| 2003/0208110 A1* | 11/2003 | Mault et al. | 600/300 |
| 2003/0208113 A1* | 11/2003 | Mault et al. | 600/316 |
| 2003/0212379 A1 | 11/2003 | Bylund et al. | |
| 2003/0217966 A1 | 11/2003 | Tapsak et al. | |
| 2003/0225324 A1* | 12/2003 | Anderson et al. | 600/364 |
| 2004/0011671 A1 | 1/2004 | Shults et al. | |
| 2004/0045879 A1 | 3/2004 | Shults et al. | |
| 2004/0054263 A1 | 3/2004 | Moerman et al. | |
| 2004/0122353 A1 | 6/2004 | Shahmirian et al. | |
| 2004/0135684 A1* | 7/2004 | Steinthal et al. | 340/522 |
| 2004/0152961 A1* | 8/2004 | Carlson et al. | 600/301 |
| 2004/0155079 A1 | 8/2004 | Shetler et al. | |
| 2004/0186362 A1 | 9/2004 | Brauker et al. | |
| 2004/0199059 A1 | 10/2004 | Brauker et al. | |
| 2004/0254434 A1 | 12/2004 | Goodnow et al. | |
| 2005/0003470 A1* | 1/2005 | Nelson et al. | 435/14 |
| 2005/0031689 A1 | 2/2005 | Shults et al. | |
| 2005/0043598 A1 | 2/2005 | Goode, Jr. et al. | |
| 2005/0090607 A1 | 4/2005 | Tapsak et al. | |
| 2005/0112169 A1 | 5/2005 | Brauker et al. | |
| 2005/0143635 A1 | 6/2005 | Kamath et al. | |
| 2005/0154271 A1* | 7/2005 | Rasdal et al. | 600/347 |
| 2005/0171512 A1 | 8/2005 | Flaherty | |
| 2005/0176136 A1 | 8/2005 | Burd et al. | |
| 2005/0182366 A1 | 8/2005 | Vogt et al. | |
| 2005/0187720 A1 | 8/2005 | Goode, Jr. et al. | |
| 2005/0192557 A1 | 9/2005 | Brauker et al. | |
| 2005/0203461 A1 | 9/2005 | Flaherty et al. | |
| 2005/0238507 A1 | 10/2005 | DiIanni et al. | |
| 2005/0239156 A1 | 10/2005 | Drucker et al. | |
| 2005/0245795 A1 | 11/2005 | Goode, Jr. et al. | |
| 2005/0245799 A1 | 11/2005 | Brauker et al. | |
| 2005/0277164 A1 | 12/2005 | Drucker et al. | |
| 2006/0010098 A1 | 1/2006 | Goodnow et al. | |
| 2006/0015020 A1 | 1/2006 | Neale et al. | |
| 2006/0016700 A1 | 1/2006 | Brister et al. | |
| 2006/0019327 A1 | 1/2006 | Brister et al. | |
| 2006/0020186 A1 | 1/2006 | Brister et al. | |
| 2006/0020187 A1 | 1/2006 | Brister et al. | |
| 2006/0020188 A1 | 1/2006 | Kamath et al. | |
| 2006/0020189 A1 | 1/2006 | Brister et al. | |
| 2006/0020190 A1 | 1/2006 | Kamath et al. | |
| 2006/0020191 A1 | 1/2006 | Brister et al. | |
| 2006/0020192 A1 | 1/2006 | Brister et al. | |
| 2006/0036139 A1 | 2/2006 | Brister et al. | |
| 2006/0036140 A1 | 2/2006 | Brister et al. | |
| 2006/0036141 A1 | 2/2006 | Kamath et al. | |
| 2006/0036142 A1 | 2/2006 | Brister et al. | |
| 2006/0036143 A1 | 2/2006 | Brister et al. | |
| 2006/0036144 A1 | 2/2006 | Brister et al. | |
| 2006/0036145 A1 | 2/2006 | Brister et al. | |
| 2006/0041229 A1 | 2/2006 | Garibotto et al. | |
| 2006/0178633 A1 | 8/2006 | Garibotto et al. | |
| 2006/0222566 A1 | 10/2006 | Brauker et al. | |
| 2006/0224141 A1 | 10/2006 | Rush et al. | |
| 2006/0226985 A1 | 10/2006 | Goodnow et al. | |
| 2006/0282290 A1 | 12/2006 | Flaherty et al. | |
| 2007/0118405 A1 | 5/2007 | Campbell et al. | |
| 2007/0163880 A1 | 7/2007 | Woo et al. | |
| 2007/0203966 A1 | 8/2007 | Brauker et al. | |
| 2007/0219480 A1 | 9/2007 | Kamen et al. | |
| 2007/0219597 A1 | 9/2007 | Kamen et al. | |
| 2007/0235331 A1 | 10/2007 | Simpson et al. | |
| 2008/0021666 A1 | 1/2008 | Goode, Jr. et al. | |
| 2008/0033254 A1 | 2/2008 | Kamath et al. | |
| 2008/0045824 A1 | 2/2008 | Tapsak et al. | |
| 2008/0071156 A1 | 3/2008 | Brister et al. | |
| 2008/0083617 A1 | 4/2008 | Simpson et al. | |
| 2008/0086042 A1 | 4/2008 | Brister et al. | |
| 2008/0086044 A1 | 4/2008 | Brister et al. | |
| 2008/0086273 A1 | 4/2008 | Shults et al. | |

FOREIGN PATENT DOCUMENTS

| | | |
|---|---|---|
| WO | WO-2004/110256 | 12/2004 |
| WO | WO-2005/119524 | 12/2005 |
| WO | WO-2006/086423 | 8/2006 |

* cited by examiner

GLUCOSE MEASURING DEVICE INTEGRATED INTO A HOLSTER FOR A PERSONAL AREA NETWORK DEVICE

FIELD OF THE INVENTION

The present invention relates to glucose monitoring devices. More particularly, the present invention relates to a glucose sensor module integrated into a holster that can accommodate another device, and further, to a method by which the glucose sensor module and the accommodated device wirelessly communicate with each other.

BACKGROUND

The number of diagnosed cases of diabetes continues to increase in the U.S. and throughout the world, creating enormous economic and public health consequences. One area in which recently developed technologies have been able to improve the standard of care has been in the maintenance of tight control over the blood glucose levels. It is well known that if a diabetic patient's blood glucose values are maintained within the normal range of from about 80 milligrams per deciliter (mg/dL) to about 120 mg/dL, the physiologically damaging consequences of unchecked diabetes can be minimized.

Recent technological and commercial development in the two areas of glucose monitoring and of insulin administration have each contributed significantly to improving the ability of diabetic people to maintain better control over their blood glucose level, and thereby enhance their quality of life.

With better blood glucose information, diabetic patients can better exercise tight control of their blood glucose level through a variety of means, including diet, exercise, and medication. A common type of glucose measuring device is represented by hand-held electronic meters which receive blood samples via enzyme-based "test strips". In using these systems, the patient lances a finger or alternate body site to obtain a blood sample, the sample is applied to the strip, the strip is inserted into a port in the meter housing where it engages the meter's internal electronics, and the electronics convert a current generated by the enzymatic reaction in the test strip to a blood glucose value. The glucose value is then typically displayed on the meter's liquid crystal display (LCD), which is generally relatively large in size in order to accommodate the eyesight capability of older adults and diabetic people, who often have deteriorating vision.

Some diabetic patients require insulin administration in order to maintain tight control of their glucose level. Insulin administration to these insulin-dependent patients has traditionally been by self-injection, but a more recently available technology is represented by insulin pumps. These pump devices offer significant therapeutic value over self injection, as the pumps deliver insulin in a more physiological manner, with measured doses of insulin being infused slowly, over an extended period of time. Further, the rate at which insulin is delivered can be programmed to follow standard or individually-modified protocols, to give the user even better glucose control over the course of a day. Insulin pumps have commercially evolved to become small in size, which offers easier portability and unobtrusiveness, and with electronic advances, they have evolved to become more fully-featured, and thus capable of enhanced and individualized performance. These various advantages in terms of health care quality and user convenience have supported the growth of the insulin pump market.

It has been recognized that combining the newer technologies of insulin administration with the newer technologies of glucose measurement could significantly improve user convenience, resulting in a greater ability to comply with frequent testing, and greater ability to effect individually appropriate schedules of insulin administration.

Such an integrated combination of a glucose measuring device and insulin pump is shown in U.S. Pat. No. 5,665,065, which teaches the inclusion of a mechanism for measuring blood glucose within the housing of an insulin pump. While the advantages of such a glucose measuring/insulin pump combinations has been known for many years, in fact, no such device has become commercially available. Various practical and market-based factors may contribute to the absence of a combination device in the market. Insulin pumps, though expensive, have become well established and stabilized in the market; and pump users tend to remain with their initial choice. Glucose meters, in contrast, are presently evolving more quickly and are inexpensive for users; indeed they are often provided to users by manufacturers without charge, as a loss leader in an overall business strategy. At least in part as a consequence of the low price, glucose meter users have lower brand loyalty, and will switch among brands. As another consequence, there is intense manufacturing cost pressure on glucose meters, which, in turn, encourages efficient product design by the meter manufacturers. From the perspective of a pump manufacturer in designing such a physically integrated combination device, the manufacturer would need to commit to a particular blood glucose measuring technology in the face of the concern that such technology could become less competitive or even obsolete during the normal life of the pump product.

It is known that hand-held glucose meters can advantageously be manufactured to include short range wireless communication capability, through which data from the glucose sensor can be transmitted to another health device, such as a computer, cell phone, or a personal digital assistant (PDA); such wireless communication between two portable devices is shown in the PCT publication WO03005891A1. This wireless data transfer relieves the glucose sensor user of the need to record such data by hand, and allows for accumulation of data points within a larger database for longer term health monitoring and intervention. In spite of the benefits of wireless communication, the inconvenience of handling separate devices to achieve the patient's singular goal of maintaining glucose control remains unsolved by wireless communication alone.

Devices that provide for secure personal portability of various communication and health-related electronic devices, and ease of use while being carried are also well known. Holsters and cases for electronic devices that attach to belts or other articles of clothing are never far from where mobile telephones are being sold, and are described in U.S. Pat. Nos. 5,664,292 and 5,833,100, and 6,081,695. Similarly, U.S. Pat. No. 5,472,317 describes an apparatus that provides for a belt-clip mounting for a medication infusion pump.

In view of these various problematic factors associated with the actual physical integration of a glucose measuring device with an insulin pump, it would be desirable to provide an insulin pump user the benefits and performance of functionally combined glucose measuring device and insulin pump. Such a combined device would desirably be in a portable configuration that, in fact, maintains physical distinctness of the devices, gets past the market-based barriers that accompany physical integration, and yet offers a combination which for all practical purposes is used as a single integrated device. It would be further desirable for this functionally integrated device to be fully enabled to interact with other devices within a personal area network.

SUMMARY OF THE INVENTION

In view of the foregoing, in accordance with one embodiment of the present invention, there is provided a glucose monitoring device housing, comprising a holster unit, a glucose sensing module integrally disposed on the holster unit, where the holster unit is configured to substantially receive a server device, the server device configured to wirelessly communicate with the glucose sensing module.

The server device may include a blood glucose monitoring device. Alternatively, the server device may include one or more of an insulin pump, a personal digital assistant, a mobile telephone, and a portable gaming unit.

The server device may be configured to receive one or more data from the glucose sensing module, the one or more data including one or more data related to a detected blood glucose level.

The glucose sensing module may include a test strip port configured to receive a test strip.

The glucose sensing module may be shaped substantially elongate.

In one embodiment, the glucose sensing module may be configured to transmit data to the server device when the server device is substantially positioned within the holster unit.

The holster unit may include in one embodiment a belt clip portion, and a device clasping portion mechanically coupled to the belt clip portion.

The belt clip portion may be mechanically coupled to the device clasping portion by a spring biased connector unit.

Further, the glucose sensing module may be integrally disposed on one of the belt clip portion and the device clasping portion.

The glucose sensing module may include a test strip port configured to receive a test strip.

The device clasping portion of the holster unit may be configured to receive the server device such that the server device is in physical contact with the device clasping portion. Moreover, the server device may be securely positioned substantially within the device clasping portion of the holster unit.

Additionally, in one embodiment, each of the glucose sensing module and the server device may include a communication port for data communication.

Indeed, the glucose sending module communication port and the server device communication port each may include one of an infrared port, a Bluetooth enabled communication port, and a Wi-Fi enabled communication port.

The server device may include in one embodiment one or more of an output unit, and an input unit, where the output unit may include one or more of a display unit and an audio output unit.

The display unit in this case may include one of a liquid crystal display (LCD) unit, a plasma display unit, and a touch-sensitive display unit, and further, wherein the audio output unit includes an output speaker.

Also, the input unit may include one or more of an input button, and a touch-sensitive input unit integrated with the output unit.

Additionally, the output unit may be configured to output one or more of an image data, a video data, and an audio signal, in response to a predetermined event.

The predetermined event in one embodiment may include one or more of an input command generated by the input unit and a detection of a glucose sensing module signal.

A method of providing a glucose monitoring device housing in accordance with another embodiment of the present invention includes the steps of providing a holster unit, integrally disposing a glucose sensing module on the holster unit, configuring the holster unit to substantially receive a server device, and configuring the server device to wirelessly communicate with the glucose sensing module.

In a further embodiment, the server device may include one or more of a blood glucose monitoring device, an insulin pump, a personal digital assistant, a mobile telephone, and a portable gaming unit.

The method may further include the step of configuring the server device to receive one or more data from the glucose sensing module, the one or more data including one or more data related to a detected blood glucose level.

Also, the method may additionally include the step of providing a test strip port on the glucose sensing module, the test strip port configured to receive a test strip.

Indeed, the method may also include the step of configuring the glucose sensing module to transmit data to the server device when the server device is substantially positioned within the holster unit.

A data management system for managing health related data in accordance with still another embodiment of the present invention includes a personal area network, a client device configured for data communication in the personal area network, and a server device configured to communicate with the client device in the personal area network, where the client device is configured to transmit one or more health related data to the server device over the personal area network, and the server device is configured to generate one or more health management signals based on the received one or more health related data.

The client device may include a client device wireless communication port for data communication, and the server device includes a server device wireless communication port for data communication.

Further, each of the client device wireless communication port and the server device wireless communication port may include one of an infrared port, a Bluetooth enabled port, and a Wi-Fi communication port.

Moreover, the client device may include a blood glucose meter, and further, where the health related data includes a blood glucose level data.

The server device may include a blood glucose monitoring device configured to generate the one or more health management signals based on the blood glucose level data received from the blood glucose meter, where the health management signals includes one or more of an audio alert signal, a vibration alert signal, and a graphical display signal.

The blood glucose monitoring device may in one embodiment be configured to generate an alert signal for output when the received blood glucose level data is determined to be beyond a predetermined range.

Also, the predetermined range may substantially establish an impending hyperglycemic state and an impending hypoglycemic state.

In the manner described above, in accordance with one embodiment of the present invention, there is provided a glucose monitoring and response system that includes a glucose meter module, operating within a personal area network as a client device, integrated into a holster apparatus typically clipped or loop-attached to a belt or other article of clothing worn by a diabetic person, the holster being configured so as to be able to securely accommodate another health device such as a portable server device or an insulin pump. Communication between the glucose measuring module and the responding health device may be performed by a wireless modality, for example using infrared (IR), Bluetooth, or Wi-Fi (801.11g, 801.11b, or 801.11a) protocols.

In one embodiment, the accommodated device may include a server, such as a personal digital assistant or cell phone, where the accommodated device may be configured to store data in a memory, display data on a visual display, and may wirelessly transmit such data to other devices within a personal area network (PAN), as well as send data to remote sites via the global system for mobile communications (GSM). In another embodiment where the health device includes an insulin pump, the wirelessly received data may be stored in a memory, and may be available for visual display on the insulin pump, as well as incorporating into the selection of appropriate protocols that regulate the performance of the pump.

The glucose measuring module in one embodiment of the present invention may include glucose measuring circuitry for enzymatic electrochemical detection of glucose in a blood sample. The module, by including a holster accommodation for a device with which it wirelessly communicates, may be configured to establish a functional system integration in spite of physical distinctness of the two major system components. Cost and size of the holster-integrated glucose meter may be minimized by reliance on the fully meter-functional display and controls present on the holster-accommodated device, and the absence of the redundant visual display and redundant control buttons on the glucose meter.

More particularly, in accordance with one embodiment of the present invention, there is provided a glucose sensing and insulin delivery system which includes a glucose sensor module, an insulin pump including a visual display, a holster apparatus into which the glucose sensor module is integrated and which holster is configured to hold the insulin pump, and a wireless data communication system for transmitting data between the glucose sensor module and the insulin pump.

In another embodiment, the holster apparatus may include a belt-clip portion and a device clasping portion. Moreover, the glucose sensor module may be integrated into the device-clasping portion of the holster apparatus. Alternatively, the glucose sensor module may be integrated into the belt-clip portion of the holster apparatus.

The wireless data communication system may include an infrared transceiver in the glucose sensor module and an infrared transceiver in said insulin pump. Additionally, the wireless data communication system may include a Bluetooth-enabled transceiver in the glucose sensor module and a Bluetooth-enabled transceiver in the insulin pump.

Furthermore, the glucose sensing and insulin delivery system may include a single visual display. Alternatively, the glucose sensor module may not include a visual display.

In addition, the insulin pump may include a housing, where the housing includes control buttons mounted in the housing.

Also, control unit may be provided for controlling the operation of the glucose module, where the control unit may include control buttons mounted on the insulin pump.

In accordance with another embodiment of the present invention, there is provided a glucose sensing system comprising a glucose sensor module enabled to wirelessly communicate within a personal area network, a second personal area network communication-enabled device including a visual display, and a holster apparatus into which the glucose sensor module is integrated and which holster is configured to hold the second personal area network device.

The second personal area network communication-enabled device may include an insulin pump. Alternatively, the second personal area network communication-enabled device may include a cell phone.

These and other features and advantages of the present invention will be understood upon consideration of the following detailed description of the invention and the accompanying drawings.

BRIEF DESCRIPTION OF THE DRAWINGS

The invention will now be described by reference to the figures, wherein like reference numerals and names indicate corresponding structure throughout the several views.

DETAILED DESCRIPTION

Figure 1A:
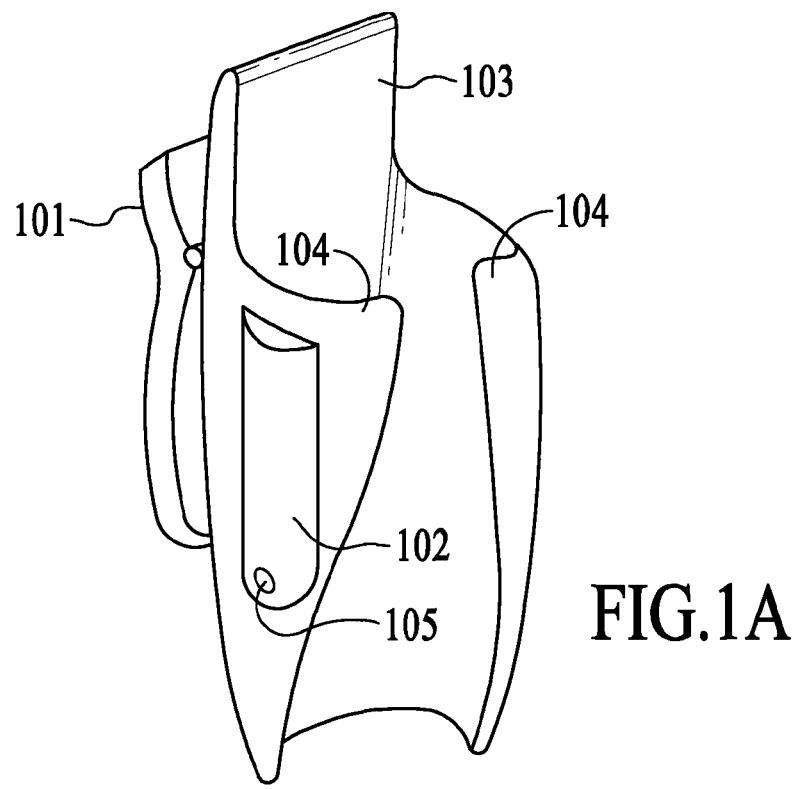
FIG. 1A illustrates a glucose measuring module integrated into the device-clasping portion in accordance with one embodiment of the present invention.

FIG. 1A illustrates a glucose measuring module integrated into the device-clasping portion in accordance with one embodiment of the present invention. Referring to the Figure, there are shown two main components of the holster apparatus, a belt-clip portion 101 and device-clasping portion 103, which includes a glucose sensing module 102, a client device within the larger context of networked devices to be further described below. The glucose-sensing module is generally elongate and pen-shaped, as has been described in U.S. patent application entitled Glucose Measuring Device for Use in Personal Area Network filed Jun. 4, 2004, assigned to TheraSense, Inc., of Alameda Calif., the assignee of the present invention, and the disclosure of which is incorporated herein by reference for all purposes. More specifically, as shown in the Figure, the glucose sensing module 102 may be integrally molded into the larger contours of the device clasping portion of the holster apparatus, and situated vertically on the outer aspect of one of the two clasping arms 104 of device clasping portion 103.

At the base of the glucose sensing module 102 is located a test strip port 105, wherein test strips are inserted after having been contacted with a blood sample. Alternatively, glucose sensing module 102 can be configured to accept test strips before they have been contacted with a blood sample. Other configurations for the placement of the glucose sensing module within the clasping portion of the holster are possible that would meet the basic requirement that the module, and more particularly the test strip port 105 within the module, be readily accessible to the user. The two holster mechanical components, the belt-clip portion 101 and the device-clasping portion 103, may be joined by a spring-biased connector (not shown) which causes the belt-clip to press toward the device-clasping portion, in order to grip a belt or article of clothing worn by a user, and thus to secure the apparatus.

Figure 1B:
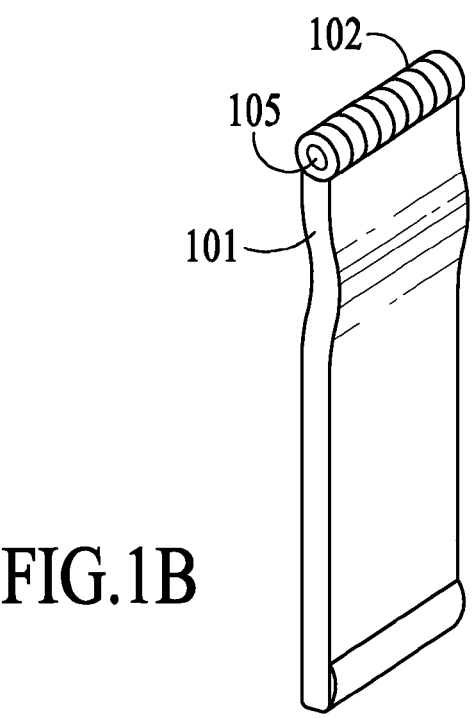
FIG. 1B illustrates a belt-clasping portion with a glucose measuring module integrated thereto in accordance with another embodiment of the present invention.

FIG. 1B illustrates a belt-clasping portion with a glucose measuring module integrated thereto in accordance with another embodiment of the present invention. Referring to the Figure, there is shown a perspective view of a belt-clip portion of another embodiment of the holster apparatus into which the glucose sensing module 102 has been integrated. As noted in the description above in conjunction with FIG. 1A, the glucose-sensing module 102 is generally elongate and pen-shaped, but in this embodiment it has been molded into the larger contours of the belt-clip portion 101 of the holster apparatus, and is situated horizontally across the top of the upper aspect thereof. Other configurations for the placement of the glucose sensing module are possible that would meet the basic desire that the module, and more particularly the test strip port 105 within the module be readily accessible to the user. Because of the constraints of the generally elongate profile of the glucose sensing module 102 as a whole, as well as the elongate profiles of test strips and the test strip port 105, the test strip port 105 in one embodiment of the present invention is preferably located at one of the two ends of the glucose sensing module 102 (see FIGS. 1A-1B and 2A-2B.). The analog "front end" circuitry associated with measuring the small electrochemical currents from test strips 101 is located near the strip port 105, and is sensitive to electrical interference. It is advisable, therefore, to situate the wireless link antenna of the glucose sensing module 102 at a such a distance from the strip port end that such wireless transmission interference does not occur. In operation, in accordance with one embodiment, the holster apparatus may either be worn by the user while the test strip is inserted into the test strip port 105, or alternatively, the holster apparatus may be removed from the user's belt, for example, when inserting the test strip into the test strip port 105 and conducting a glucose measurement.

Figure 2A:
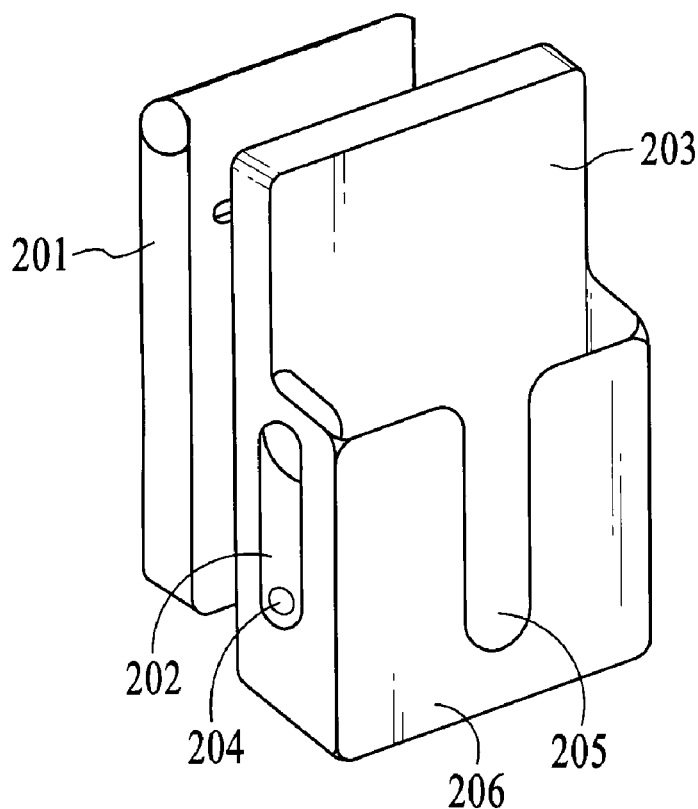
FIG. 2A illustrates a glucose measuring module integrated into the device-clasping portion in accordance with another embodiment of the present invention.

FIG. 2A illustrates a glucose measuring module integrated into the device-clasping portion in accordance with another embodiment of the present invention. Referring to the Figure, there are shown the two main components of the holster apparatus, a belt-clip portion 201 and device-clasping portion 203, which includes a glucose sensing module 202, a client device within the larger context of networked devices as described in further detail below. This embodiment illustrates features that provide both for swiveling of the held device with respect to the relatively fixed orientation of the holster when secured to a belt, as well as an ability to quickly engage and disengage the held server device (see FIG. 4) from the holster. The feature providing these forms of functionality is a button-holding box 206, which includes a U-shaped slot 205. Fitting into this U-shaped slot 205 is a complementary broadened holding button 407 (see FIG. 4) that is attached to the back of the held server device 411 (see FIG. 4), thereby securing the held server device 411 to the holster.

Referring back to FIG. 2A, the glucose-sensing module 202, generally elongate and pen-shaped, may be molded into the larger contours of the device clasping portion 203 of the holster apparatus, and may be situated vertically on the outer aspect of one of the two sides of the clasping portion 203 of the holster, or on one of the sides of the button-holding box 206. Located at the base of the glucose sensing module 202 may be a test strip port 204, into which test strips are inserted before or after having been contacted with a blood sample. Other configurations for the placement of the glucose sensing module within the clasping portion of the holster are possible that would meet the basic requirement that the module, and more particularly the test strip port 204 within the module be readily accessible to the user. The two major mechanical components of the holster, the belt-clip portion 201 and the device-clasping portion 203, are typically joined by a spring-biased connector (not shown) which causes the belt-clip to press toward the device-clasping portion 203, in order to grip a belt or an article of clothing worn by a user, and thus to secure the apparatus.

Figure 2B:
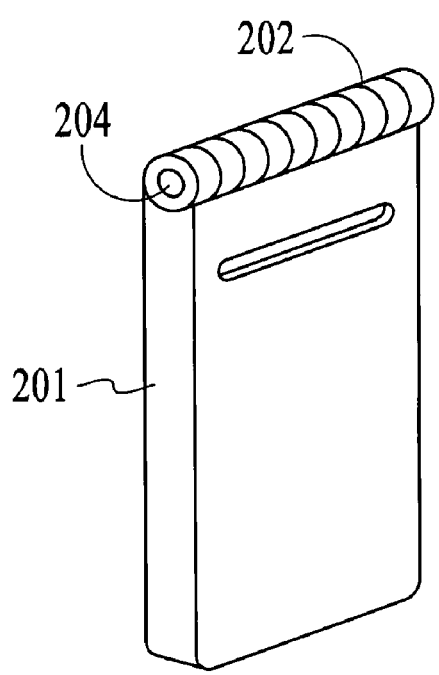
FIG. 2B illustrates the belt-clasping portion with a glucose measuring module integrated therewith in accordance with another embodiment of the present invention.

FIG. 2B illustrates the belt-clasping portion with a glucose measuring module integrated therewith in accordance with another embodiment of the present invention. Referring to the Figure, there is shown a perspective view of a belt-clip portion 201 of another embodiment of the same general type of holster apparatus as seen in FIG. 2A, into which the glucose sensing module 102 has been integrated. As discussed above in conjunction with FIG. 2A, the glucose-sensing module 102 is generally elongate and pen-shaped, but has been molded into the larger contours of the belt-clip portion 201 of the holster apparatus, and situated horizontally across the top of the upper aspect of the belt-clip portion 201 of the holster apparatus. Within the scope of the present invention, other configurations for the placement of the glucose sensing module are possible that would meet the basic desire that the module, and more particularly the test strip port 204 within the module be readily accessible to the user.

Moreover, other forms of the belt-clip portion of the holster may be compatible with the various embodiments shown herein and within the scope of the above-described and illustrated embodiments of the present invention. The clip, for example, may be made of bent metal or molded plastic, the clasping pressure of the spring, as described above, in these alternative embodiments being instead provided by the spring bias inherent in the bent metal or molded plastic. Metal clips may also be covered with fabric and/or padding material. Alternatively, the belt-clip portion could also be fabricated as a loop, constructed from various materials (fabric, synthetics, leather), into which the belt of the user is threaded, and the loop could also make use of Velcro®-type hook and loop connections.

Figure 3:
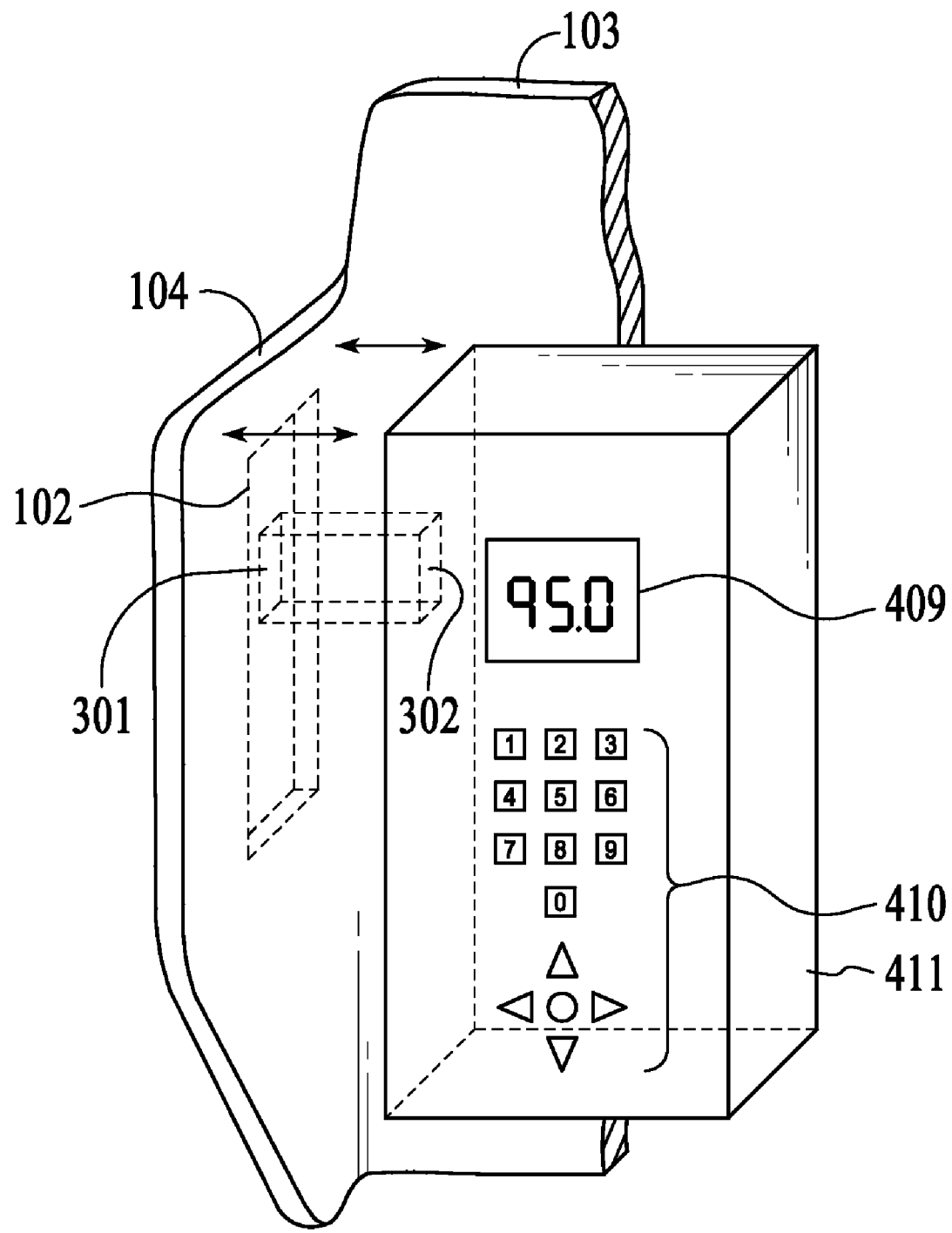
FIG. 3 illustrates a cut away perspective view where the IR transceiver ports of the glucose measuring module and the held device, respectively, are aligned for transmission of IR data in accordance with one embodiment of the present invention.
Figure 4:
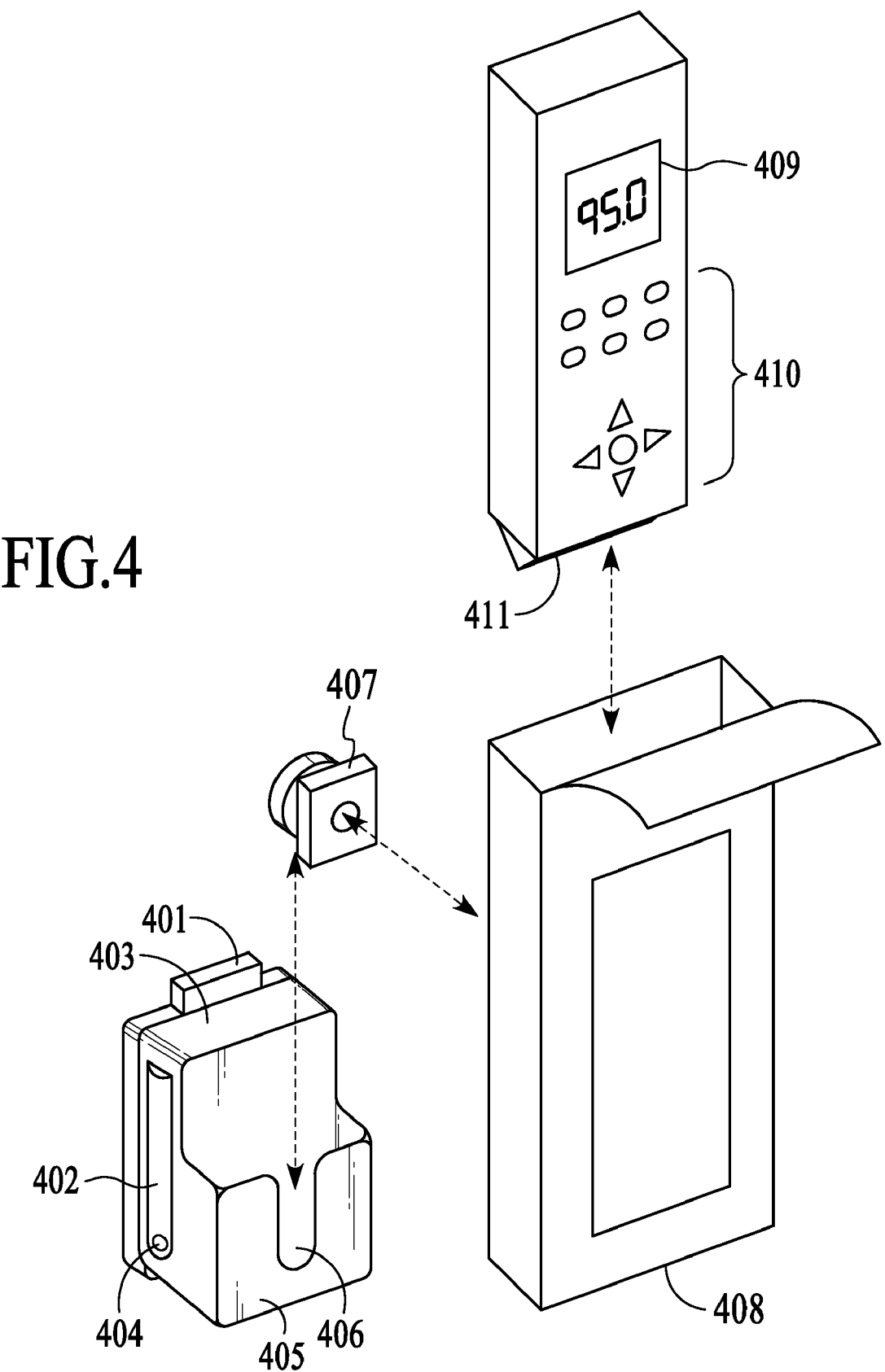
FIG. 4 illustrates an exploded view of a swivel-enabled and detachable holster apparatus, a holding button, a device carrying case, and a held server device in accordance with one embodiment of the present invention.

FIG. 3 illustrates a cut away perspective view where the IR transceiver ports of the glucose measuring module and the held device, respectively, are aligned for transmission of IR data in accordance with one embodiment of the present invention. Referring to the Figure, the infrared (IR) modality is shown as being used to transmit data between a client device and the server device 409 (FIG. 4). Successful transmission by the IR may be facilitated by a physical alignment of the transmitting and receiving data ports, as shown herein. In this exploded and partially cutaway figure, the inner aspect of a clasping arm 104 of the clasping portion 103 of a holster is shown. From this inside-looking-out and transparent perspective, the outline of the client device, or glucose sensing module 102 on the outer aspect of the clasping arm 104 is seen. Within that outline of the glucose sensing module can also be seen the wireless transceiver port 301 of the glucose sensing module, which faces inward, toward the accommodated server device 411.

Exploded rightward for visibility is the server device 411, or insulin pump in this depiction, that may be held by the holster apparatus. On the front aspect of the housing of this device, the LCD 409 and interface control keys 410 can be seen. The front aspect housing of the device 411 is for purpose of illustration rendered as partially transparent so as to make visible the transceiver port 302 of the device, located on a side wall of the housing, facing outward toward the clasping arm 104, and more specifically, toward transceiver 301 of the glucose monitor 102. It can thus be seen that when the insulin pump or portable server device 411 is contained within the holster, the two transceiver ports 301 (of the client device) and 302 (of the server device), are directly aligned together, a configuration that assures successful transmission of data by IR.

FIG. 4 illustrates an exploded view of a swivel-enabled and detachable holster apparatus, a holding button, a device carrying case, and a held server device in accordance with one embodiment of the present invention. Referring to the Figure, there is shown on the left side of the figure is a holster device, swivel-enabled and detachable, as in FIG. 3. Moving rightward, a holding button 407 is depicted. The holder button 407 is attached to the back of device carrying case 408. The button 407 is seen in this embodiment to include two basic elements (a round insertion piece and a square backing nut), connected by a spacer bar (not shown). The round insertion piece slips into the U-shaped slot of the button holder box, and secures the device carrying case 408 to the holster.

The server device in the illustrated case includes an insulin pump with an LCD display 409 and control interface keys 410. The carrying case 408 is a component of holster devices and which allows for the secure holding of a device, the device itself being unencumbered by specific attachment elements. A carrying case can be combined with the herein described holster apparatus, whether it is of the variety depicted in FIG. 1, or in FIG. 2 (swivel-enabled, detachable), as well as other variations of holsters based on two basic mechanical elements, a belt-clip portion and a device-clasping portion within the scope of the present invention. In the variations containing a case, the device-clasping portion actually secures the case, and the case, in turn, secures the held device. The case itself generally constructed from one or more types of fabric, such as cloth, plastic, or leather, and is custom fitted to the contours of the held device.

Figure 5:
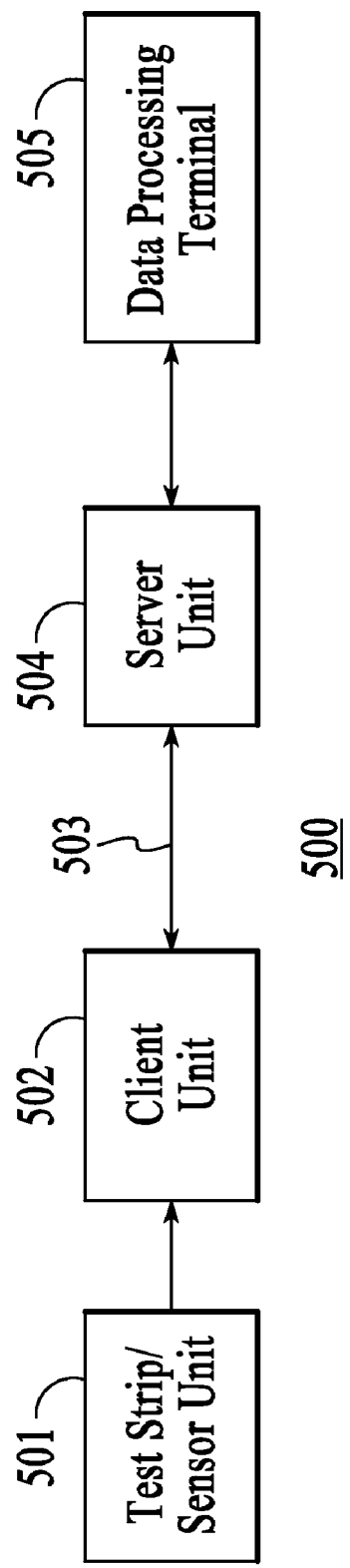
FIG. 5 is a block diagram illustrating data signal flow between devices of a wireless system in accordance with one embodiment of the present invention.

FIG. 5 is a block diagram illustrating data signal flow between devices of a wireless system in accordance with one embodiment of the present invention. Referring to the Figure, a wireless system 500 for moving data among devices in the context of a personal area network and constructed according to one embodiment of the present invention is shown. In one embodiment, the test strip 501 electrically communicates with client device 502, which wirelessly communicates with server device 504, such as by two-way radio frequency (RF) contact, infrared (IR) contact, or other known wireless connections 503. Optionally, server device 504 may also communicate with other devices such as data processing terminal 505 by direct electronic contact, via RF, IR, or other wireless connections.

Test strip/sensor unit 501 is an electrochemical analyte test strip, such as the blood glucose test strip described in U.S. patent application Ser. No. 09/434,026 filed Nov. 4, 1999 entitled "Small Volume In Vitro Analyte Sensor and Methods", assigned to TheraSense, Inc., of Alameda, Calif., the assignee of the present invention, and the disclosure of which is incorporated herein by reference for all purposes. The test strip 501 is mechanically received in a test strip port 105, 204, 404 (of the embodiments shown in FIGS. 1, 2, and 4, respectively) of a client device 502, similar to a hand-held blood glucose meter as described in the aforementioned patent application entitled Small Volume In Vitro Analyte Sensor and Methods. In one embodiment, client device 502 is constructed without a user interface or display to keep the size and cost of device 502 to a minimum. Client device 502 can be powered by a single AA or AAA size battery, and can take a pen-like form that is integrally molded into the larger configuration of a holster, as shown in FIGS. 1 and 2.

Referring back to FIG. 5, the client device 502 wirelessly communicates with server device 504, preferably using a common standard such as 802.11 or Bluetooth RF protocol, or an IrDA infrared protocol. The server device 504 may include another portable device, such as a Personal Digital Assistant (PDA), a cell phone, a pump for a medication such as insulin, and a portable gaming unit, for example, (and as shown by some of the examples in FIG. 8). In one embodiment, the server device 504 includes a display, such as a liquid crystal display (LCD), as well as an input device, such as control buttons, a keyboard, mouse or touch-screen. With this configuration, the user can control client device 502 via interaction with the user interface(s) of server device 504, which in turn interacts with client device 102 across wireless link 503.

The server device 504 may also communicate with a data processing terminal 505, such as for sending glucose data from devices 502 and 504, and/or receiving instructions or an insulin pump protocol from a health care provider via the data processing terminal 505. Examples of such communication include a PDA 504 synchronizing data with a personal computer (PC) 505, a mobile phone 504 communicating over a cellular network with a computer 505 at the other end, or an insulin pump 504 communicating with a computer system 505 at a physician's office.

Figure 6:
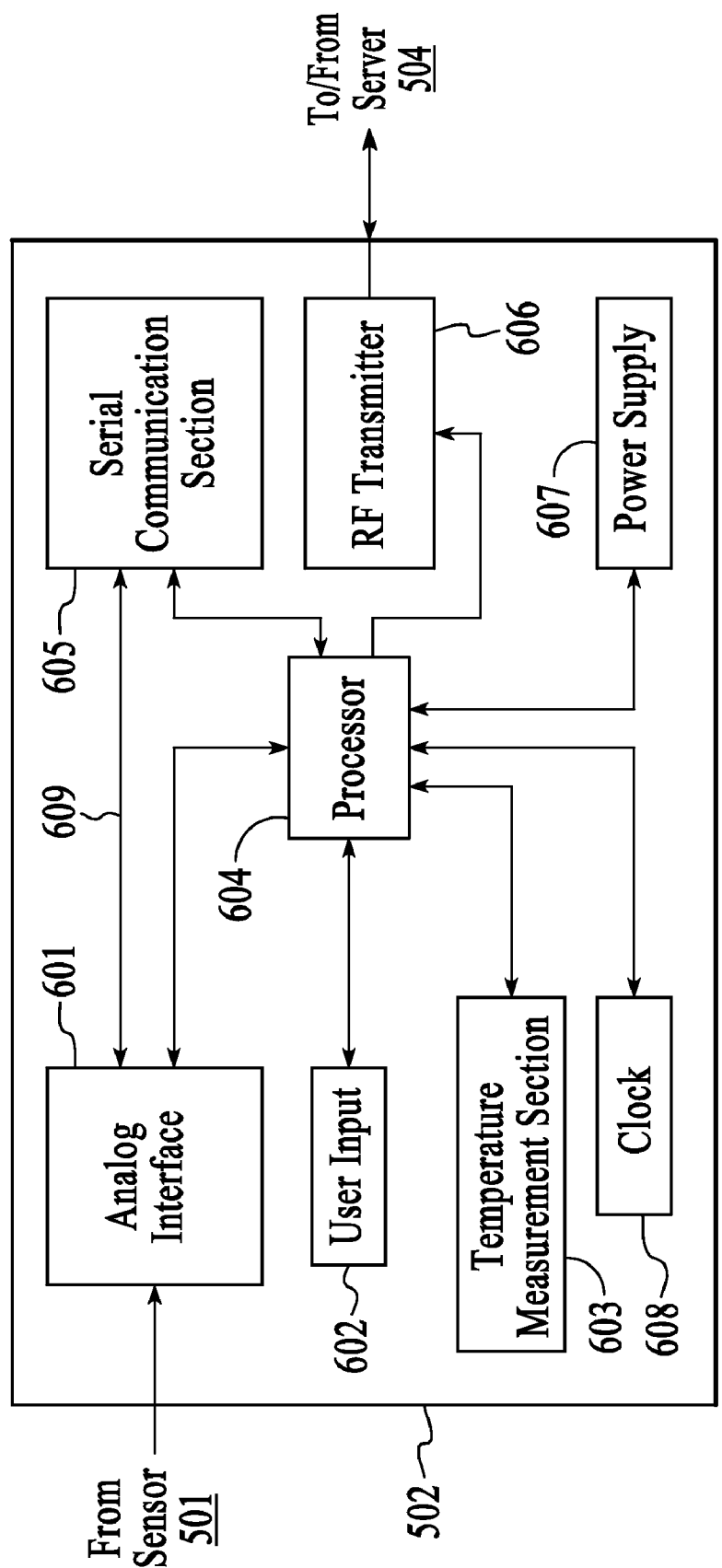
FIG. 6 is a block diagram of a glucose meter client device as shown in FIG. 3 in accordance with one embodiment of the present invention.

FIG. 6 is a block diagram of a glucose meter client device as shown in FIG. 3 in accordance with one embodiment of the present invention. Referring to FIG. 6, internal components of the client device 502 such as a blood glucose meter of one embodiment is shown. User input 602 of data or instructions, via keys or control buttons is shown as an option, but can also be eliminated to reduce size and cost of client device 502. In this case, data or instructional input can be provided via the server device 504 held in the holster (see FIG. 7 and description below). The glucose meter housing may contain any glucose sensing system of the type well known in the art that can be configured to fit into a small profile. Such a system can include, for example, the electrochemical glucose strip and meter sensing system sold by TheraSense, Inc. of Alameda, Calif. under the FreeStyle® brand, or other strip and meter glucose measuring systems. The housing may thus encompass the sensor electronics and a strip connector, which connector is accessed via a test strip port opening in the housing. The housing will typically also include one or more batteries.

Figure 7:
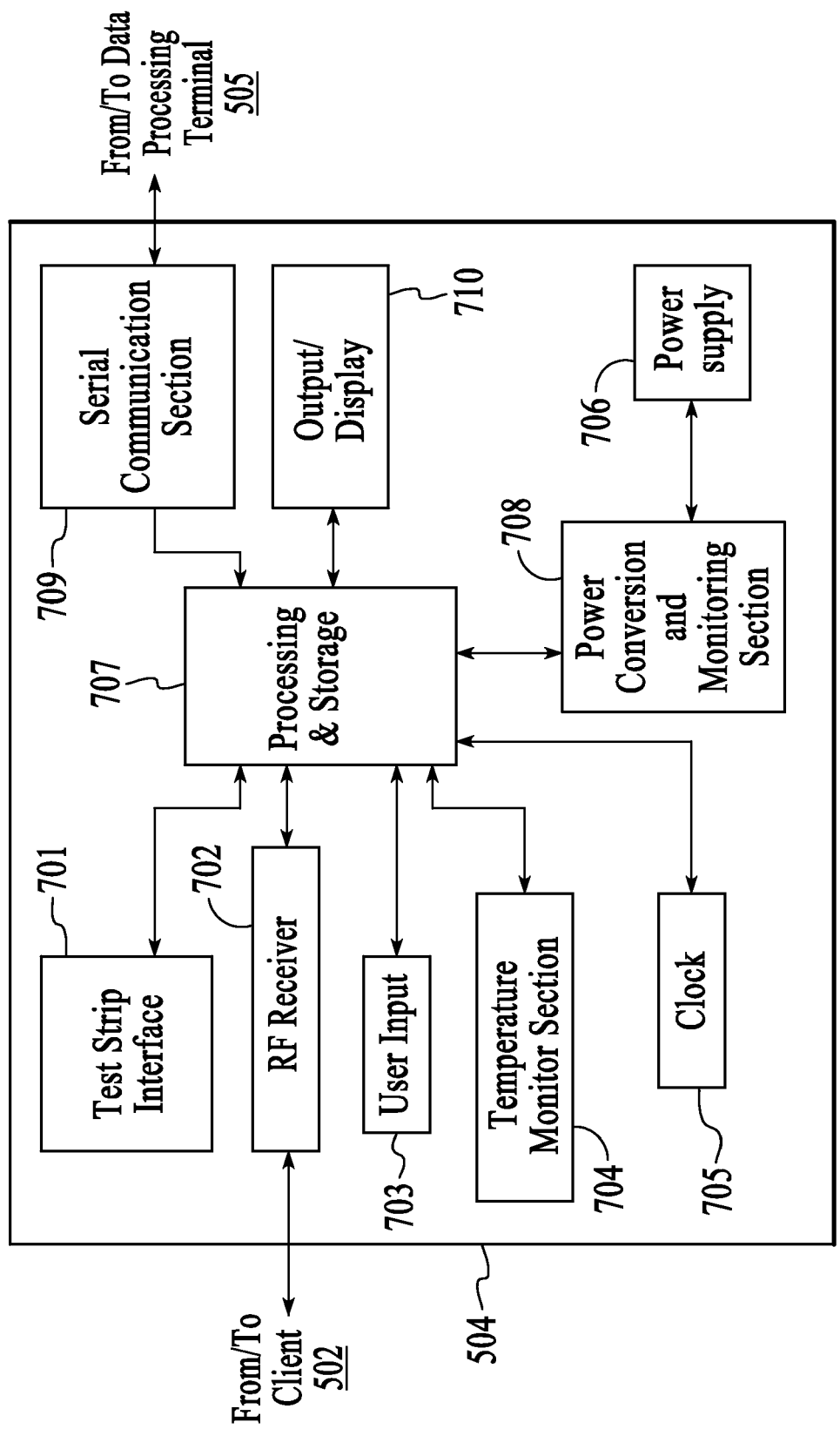
FIG. 7 is a block diagram of a server device such as an insulin pump, as shown in FIG. 3 in accordance with one embodiment of the present invention.

FIG. 7 is a block diagram of a server device such as an insulin pump, as shown in FIG. 3 in accordance with one embodiment of the present invention. Referring to FIG. 7, internal components of server device 504 of one embodiment are shown. Note that a redundant test strip interface 701 can be provided if desired for receiving test strips 501. Server device 504 can be a proprietary unit designed specifically for use with blood glucose meters, or can be a generic, multipurpose device such as a standard PDA. An example of a similar device designed for blood glucose testing is disclosed in U.S.

Pat. No. 6,560,471 issued May 6, 2003 to the TheraSense, Inc. of Alameda, Calif., the assignee of the present invention, entitled "Analyte Monitoring Device and Methods of Use", the disclosure of which is incorporated herein by reference for all purposes. Note also the presence of user input 703, which would occur through user manipulation of buttons or keys. There is two-way data flow between devices 502 and 504, and thus data or instructional input applied through the held device 504 can be seamlessly applied to controlling the operation of a client device (a glucose meter, for a specific example).

As noted in the discussion above of the client device in conjunction with FIG. 6, one embodiment of the present invention include the "displayless" glucose meter unit on the display of a separate device in order to minimize the complexity and cost of the meter unit. The glucose meter user "reads" and interacts with the meter via the larger display units within his or her personal area network, all of which can be synchronized as they interact and communicate with the wireless enabled meter. When the glucose meter is used, the sequences through which the user must "step" to complete the test are readily viewed on the larger display units (for example, by entering the calibration code, prompting application of the sample). At the same time the meter unit is simplified, smaller and less expensive to manufacture.

Additionally, control buttons that are found on typical glucose meters can be eliminated, saving additional size and cost, since the user can rely on the user in out features of the server device instead. It is expected that the simplified, wireless enabled meters integrated into a device holster, as described herein, may ultimately become inexpensive enough to make them disposable after a specified number of uses, permitting the producer to routinely upgrade as appropriate.

Further, the system permits the user to include security coding at any time the meter unit accesses a display device, so that the user's data are secure, such that, when the "client" meter of one embodiment of the present invention is used, the system requires the user to enter an identity code in order to verify that the person handling the meter is indeed an authorized user. In an alternate embodiment, it is possible for the system to permit more than one user if the meter owner so desires.

While the glucose sensing module does not include a large or expensive display, it may nevertheless be advantageous to include some ability to advise the user of a glucose level which is determined when the module is used as a "stand-alone" unit. For example, the module could include a very low cost, small three digit LCD display. Alternatively, the module could include light emitting diode (LED) indicator lights (for example, red for out of desired range, green for within desired range). Other possibilities include a red LED for below range, a green LED for within range, and a yellow LED for above range, or a column of LEDs or an electroluminescent strip (similar to those used on common batteries to indicate battery life) to indicate approximate or relative glucose levels.

Figure 8:
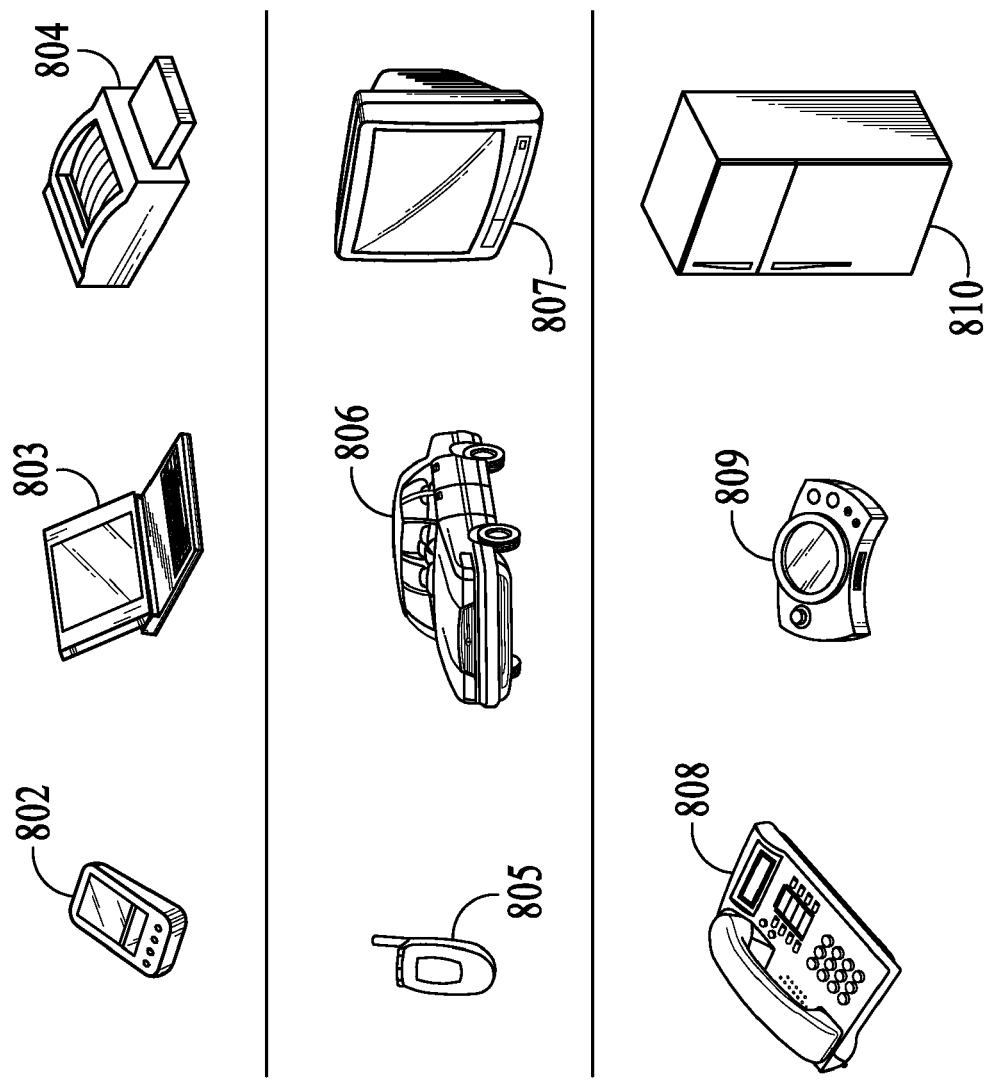
FIG. 8 is a pictorial view showing a client device and server devices within a personal area network in accordance with one embodiment of the present invention.

FIG. 8 is a pictorial view showing a client device and server devices within a personal area network in accordance with one embodiment of the present invention. More specifically, FIG. 8 shows examples of the devices to and from which the meter (client device 801) of one embodiment of the present invention can communicate. Such devices may be a part of an individual's personal area network and each device is enabled to communicate via short range wireless communication link with every other device. Laptop computers 803 and handheld computers 802, as well as printers 804 can be so enabled and will provide displays and printouts valuable as records for the diabetic. Telephones such as cellular telephones 805 and regular land-line telephones 808 will also be enabled in this fashion and can be used for displaying glucose data as well as further enabled to transmit the data over larger networks via GSM protocols (as for the cellular telephones 805). Many of these devices can assist the diabetic by responding to glucose levels by providing alarms, or suggesting that action be taken to correct a hypoglycemic or hyperglycemic condition, or by summoning necessary medical assistance.

Diabetics are well aware of the risks involved in driving when glucose levels are out of range and particularly when they are too low. Thus, for example, the navigation computer in the diabetic's vehicle 806 could become part of the personal area network and would download glucose data from the meter when the diabetic enters the vehicle 806. For the sake of safety, the car computer system could be programmed to require that the diabetic perform a glucose test before driving, and more specifically the car could be disabled until the diabetic performs a blood glucose test and the result is in an appropriate range. Other possible devices for communication with the client device 801 may include a television 807, a gaming device 809, and a refrigerator 810.

In this manner, in accordance with the embodiments of the present invention, there is provided a glucose monitoring system resulting from the functional combination of a holster-integrated glucose measuring device and a second device accommodated within the holster. The holster itself includes a belt-clip portion and a device-clasping portion; the glucose monitor can be integrated into either portion. Various embodiments provide for an ability for the belt-clip and device-clasping portions to swivel with respect to each other, and to detach from each other. In the embodiments where the belt-clip portion and clasping portion do not detach, the clasping portion provides for a quick attachment/detachment of the held server device.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A data management system for managing health related data, comprising:
   a personal area network;
   a client device having no user interface component and configured for data communication in the personal area network, said client device having a clasp portion with a port provided on an outer surface of the clasp portion to receive a medical component with an analyte sample; and
   a server device configured to communicate with the client device in the personal area network;
      wherein the client device is configured to transmit one or more health related data to the server device over the personal area network, and the server device is configured to generate one or more health management signals based on the received one or more health related data;
      wherein the server device is configured to detachably couple to the clasp portion of the client device such that the server device is in physical contact with an inner surface of the clasp portion when coupled to the clasp portion, the inner surface of the clasp portion defining an opening to receive the server device;

wherein the client device includes a client device wireless communication port for data communication, and the server device includes a server device wireless communication port for data communication; and wherein the port of the client device includes a strip port and further, wherein the medical component includes an in vitro blood glucose test strip.

2. The system of claim 1 wherein each of the client device wireless communication port and the server device wireless communication port includes one of an infrared port, a radio frequency enabled port, and a Wi-Fi communication port.

3. The system of claim 1 wherein the client device includes a blood glucose meter, and further, wherein the health related data includes a blood glucose level data.

4. The system of claim 3 wherein the server device includes a blood glucose monitoring device configured to generate the one or more health management signals based on the blood glucose level data received from the blood glucose meter.

5. The system of claim 4 wherein the one or more health management signals includes one or more of an audio alert signal, a vibration alert signal, and a graphical display signal.

6. The system of claim 4 wherein the blood glucose monitoring device is configured to generate an alert signal for output when the received blood glucose level data is determined to be beyond a predetermined range.

7. The system of claim 6 wherein the predetermined range substantially establishes an impending hyperglycemic state and an impending hypoglycemic state.

8. The system of claim 1 wherein the server device includes one or more of a personal digital assistant, a cell phone, a portable gaming unit, an insulin pump, or one or more combinations thereof.

9. The system of claim 1 wherein the outer surface and the inner surface of the client device are substantially on opposite sides.

10. The system of claim 1 wherein the clasp portion is configured to securely retain the server device when received substantially within the opening.

11. The system of claim 1 wherein the server device includes an output unit to output the generated one or more health management signals.

12. The system of claim 11 wherein the output unit of the server device is configured to output the generated one or more health management signals substantially in real time when the one or more health related data is received from the client device.

13. The system of claim 1 wherein when the medical component is provided to the port, the client device configured to process the analyte sample to generate a corresponding analyte related data.

14. The system of claim 1 wherein when the server device is received within the opening of the client device, operation of the client device is at least in part controlled by the operation of the server device.

15. The system of claim 1 wherein the server device includes a user interface which is user accessible when the server device is received within the opening of the client device.

16. The system of claim 15 wherein the client device is controlled at least in part by manipulation of the user interface of the server device.

17. The system of claim 15 wherein one or more client device control signals are received exclusively by the user interface of the server device.

18. The system of claim 17 wherein the one or more client device control signals are received when the server device is positioned in the opening of the client device.

19. A data management system for managing health related data, comprising:

a personal area network;

a client device having no user interface component and configured for data communication in the personal area network, said client device having a clasp portion with a port provided on an outer surface of the clasp portion to receive a medical component with an analyte sample; and a server device configured to communicate with the client device in the personal area network;

wherein the client device is configured to transmit one or more health related data to the server device over the personal area network, and the server device is configured to generate one or more health management signals based on the received one or more health related data;

wherein the server device is configured to detachably couple to the clasp portion of the client device such that the server device is in physical contact with an inner surface of the clasp portion when coupled to the clasp portion, the inner surface of the clasp portion defining an opening to receive the server device;

wherein the client device includes a client device wireless communication port for data communication, and the server device includes a server device wireless communication port for data communication; and wherein the client device further includes a clip portion pivotally coupled to the clasp portion such that when the server device is received in the opening of the clasp portion, the server device and the clasp portion are simultaneously moved pivotally in the same direction relative to the clip portion.

* * * * *